United States Patent [19]

Gluck

[11] Patent Number: 5,386,831
[45] Date of Patent: Feb. 7, 1995

[54] REMOTE NONINVASIVE PATIENT TEMPERATURE MONITOR AND WARNING SYSTEM

[76] Inventor: Lewis Gluck, 14 Fox Run, Wappingers Falls, N.Y. 12590

[21] Appl. No.: 209,570

[22] Filed: Mar. 11, 1994

[51] Int. Cl.⁶ ............................................... A61B 6/00
[52] U.S. Cl. ..................................... 128/664; 128/736
[58] Field of Search ................................ 128/664, 736

[56] References Cited

U.S. PATENT DOCUMENTS

| | | | |
|---|---|---|---|
| 3,287,559 | 11/1966 | Barnes | 128/736 X |
| 3,374,354 | 3/1968 | Hood | 128/736 X |
| 4,275,741 | 6/1981 | Edrich | 128/736 X |
| 4,350,166 | 9/1982 | Mobarry | 128/664 |
| 4,738,266 | 4/1988 | Thatcher | 128/664 X |

Primary Examiner—Angela D. Sykes
Attorney, Agent, or Firm—Martin J. Spellman, Jr.

[57] ABSTRACT

An infrared temperature detecting transducer and warning system is mounted on a pan-tilt mechanism that allows the temperature monitoring transducer to stay focused on the portion of a body which is particularly intended for temperature measurement. The pan-tilt mechanism has adjustable limit switches which control the range of motion of both pan and tilt and reverse the respective driving direction of each as the corresponding limit switch is tripped. A remote control processing unit receives temperature information from the infrared transducer, and stores a first temperature value and a second higher temperature value. A signal from the processing unit interrupts the power to the pan-tilt mechanism when the first temperature value is reached and connects the power when a lower temperature is not detected.

1 Claim, 2 Drawing Sheets

REMOTE NONINVASIVE PATIENT TEMPERATURE MONITOR AND WARNING SYSTEM

BACKGROUND OF THE INVENTION

1. Field of the Invention

The present invention is directed to an apparatus method for providing a constant non-invasive monitoring of an infant's body temperature in its crib. It also is able to detect changes in the temperature and if such changes exceed a predetermined, selected range, sound an alarm to attending personnel. The device of the invention also provides a means of continuously tracking and recording an infant's temperature at predetermined time intervals.

In the pediatric care environment it is usually essential that a sick infant's temperature be closely monitored and that any significant changes in the temperature be detected as soon as possible. Such changes of temperature often indicate a critical shift in the patient's condition. Effective monitoring of temperature changes requires labor intensive activity measuring the temperature by conventional and invasive means which often disturb and irritate the pediatric patient, interfering with much needed rest and sleep. In addition, the thermometers often are subject to significant instrumentation error.

Recent developments have provided less invasive means of measuring infant and other patient temperatures that are determined by simple external contact means. Even with these devises however, instrument error is still a significant factor. Furthermore, the contact is still disturbing to the pediatric patient even when less invasive instrument means are utilized.

Recently, there have been instruments developed capable of measuring the surface temperature of objects and of human beings by utilization of infrared energy, often in a form of an infrared device or gun that is aimed at the surface of the subject.

These devices have been subject to error in the cases where the infrared beam contacts background surfaces which interfere with the accurate reading of the target surface temperature desired to be measured. Such errors have been minimized by providing the infrared temperature transducer with a pulse setting light beam to target the area to be measured, giving a positive indication of the orientation of the infrared energy being utilized and the temperature measurement operation.

Instrumentation theory and practice teach that all instruments, in order to measure a quantity, must either consume or divert a small portion of that quantity in the process of measurement. This act disturbs the original quantity, altering its magnitude, and since it is the altered magnitude that is actually measured, an erroneous reading results.

This error-producing process applies to all known temperature measuring instruments except infrared thermometers. All conventional thermometers require a probe to touch the object being measured, which is usually at a different temperature. Consequently heat transfer occurs between the probe and the object until equilibrium occurs. After equilibrium occurs, the temperature measurement is said to have "come up," but the object is now either colder or warmer than it was before the probe "invaded" it. The amount by which the object is cooler or warmer than the probe is a part of the error of measurement.

Infrared thermometers produce no "invasive error." A hot object "target" is radiating its infrared radiation in all directions whether or not the infrared thermometer is there taking its temperature. The object's radiation characteristics, and hence its temperature, are not disturbed by the presence of the infrared thermometer.

The purpose of the present invention is to provide a patient, especially a pediatric patient, temperature monitoring alarm system which is completely noninvasive and does not require manual operation by medical personnel attending the patient. Means are provided for temperature monitoring or detecting and the device automatically follows an infant which is a moving target, unrestricted in its crib or other sleeping area.

This is accomplished by providing an infrared temperature detecting transducer mounted above the infant's sleeping area. The device is mounted on a pan/tilt mechanism that allows the temperature monitoring transducer to stay focused on the portion of the body of the infant which is particularly intended to measure the surface temperature thereof; i.e. forehead, back, etc. even as the infant moves about the crib. Electronic means are provided to record the temperature at predetermined times and also to signal an alarm when a sudden rise or fall in temperature is detected and/or when the surface temperature rises or falls to a predetermined absolute level.

2. Prior Art

Infrared temperature transducers of the type utilized in the present apparatus are commercially available from Everest Interscience, Inc.

U.S. Pat. No. 4,738,266, Thatcher discloses a utilization of infrared detectors and radiators mounted on a pediatric crib to detect apnea. In this case, the absence of infant breathing and the exhaling of carbon dioxide which absorbs infrared radiation is utilized to detect a sudden cessation of breathing on the part of the pediatric patient, we associate with S.I.D. (sudden infant death syndrome). Thus, when a rise in the infrared energy present is detected, an alarm is sounded to indicate a decrease or cessation in the amount of carbon dioxide exhaled by the infant.

A similar earlier system is shown on U.S. Pat. No. 4,350,166, Mobarry. None of these devices measure temperature nor do they track or scan a target surface around the specified crib area. They monitor the whole area.

Pan/tilt mechanisms for security video cameras are well known in the prior art are adapted herein for scanning the intended target with an infrared transducer.

SUMMARY OF THE INVENTION

The present invention provides a continuous automatic means for noninvasive monitoring of the temperature of a patient, especially a pediatric patient who is free to move about in his or her crib area. The temperature monitoring apparatus is mounted above the crib area on a suitable conventional mounting base with a pan/tilt mechanism that receives electronic signals from the monitoring mechanism and locks on to the target patient in the defined crib area automatically. Means are provided to acquire the target, locate the target, and to determine when any temperature change exceeds a certain predetermined rate and/or when the temperature reaches a predetermined absolute value. In either case an alarm is set off for attending personnel to check on the situation.

This invention comprises a remote noninvasive patient temperature monitor and warning system including an infrared temperature transducer, a pan/tilt motor mechanism on which said infrared temperature transducer is mounted. The pan/tilt motor mechanism has adjustable limit switches to control the range of motion of both pan and tilt and to reverse the respective driving direction of each as the corresponding limit switch is tripped. A remote control central processing unit receives temperature information from the infrared transducer, and the processing unit has means to store a first temperature value, and a second higher temperature value. A signal from the central processing unit interrupts the power circuit to the pan/tilt motors when said first temperature is reached and connects it when a lower temperature is not detected. An electronic switch device operable by the central processing unit connects a power source to a radio-transmitter or other alarm tripping device when said second temperature is detected.

BRIEF DESCRIPTION OF THE DRAWING

In the accompanying drawing which forms a part of this specification.

ILLUSTRATIVE SPECIFIC EMBODIMENT

Figure 1:
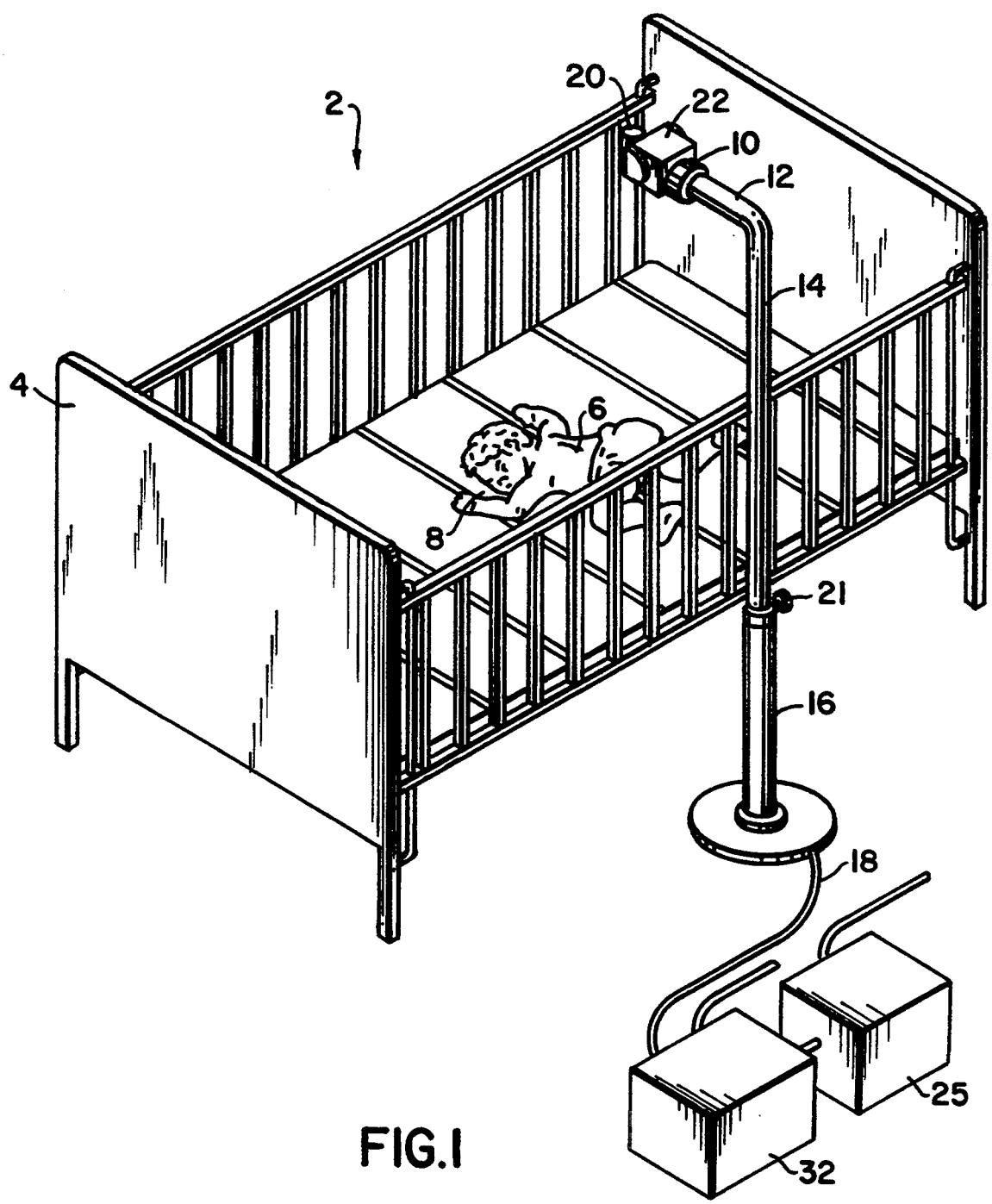
FIG. 1 is a perspective view of the apparatus of the present invention mounted over an infant's crib.

In the accompanying drawing which forms a part of this specification, the system is indicated in general by numeral 2 mounted next to a crib 4 in which the infant patient 6 is confined as shown. Normally the infant's head area 8 is the target upon which the infrared monitoring beam transducer 20 is focused. The pan/tilt mechanism is mounted on horizontal cross arm 12 which extends over the crib 4 and in turn is secured to an upright support 14 slidingly and adjustably mounted within the base sleeve 16 secured to the base or floor mounting 18 in a conventional manner. The support 14 is held at the desired position in sleeve 16 by the usual adjusting screw arrangement 21. The rotational connection 22 is provided and extending therefrom is a tilt section 22 on which the temperature monitor transducer 20 is secured. The infrared transducer 20 is mounted on a side of the section 22 and is initially manually roughly focused on the target area 8. Thereafter, the electronics direct the pan/tilt mechanism to follow a path over the target area of the crib 4. The area is defined by limit switches on the pan/tilt mechanism that are manually set.

The transducer 20 utilized is a Model 4000 A available from Everest Interscience, Inc. of Fullerton Calif. At a distance of approximately 4 feet from the infrared transducer, the field of view is about 2–3 inches in diameter. The temperature information from the transducer 20 is fed through wires 18 to a microcomputer based remote terminal 32. A suitable terminal 32 is available from Everest Interscience, Inc. and is powered by transformer 31.

The pan/tilt drive is available from Pelco, 300 West Pontiac Way, Clovis, Calif., Model PT 270 P.

Figure 2:
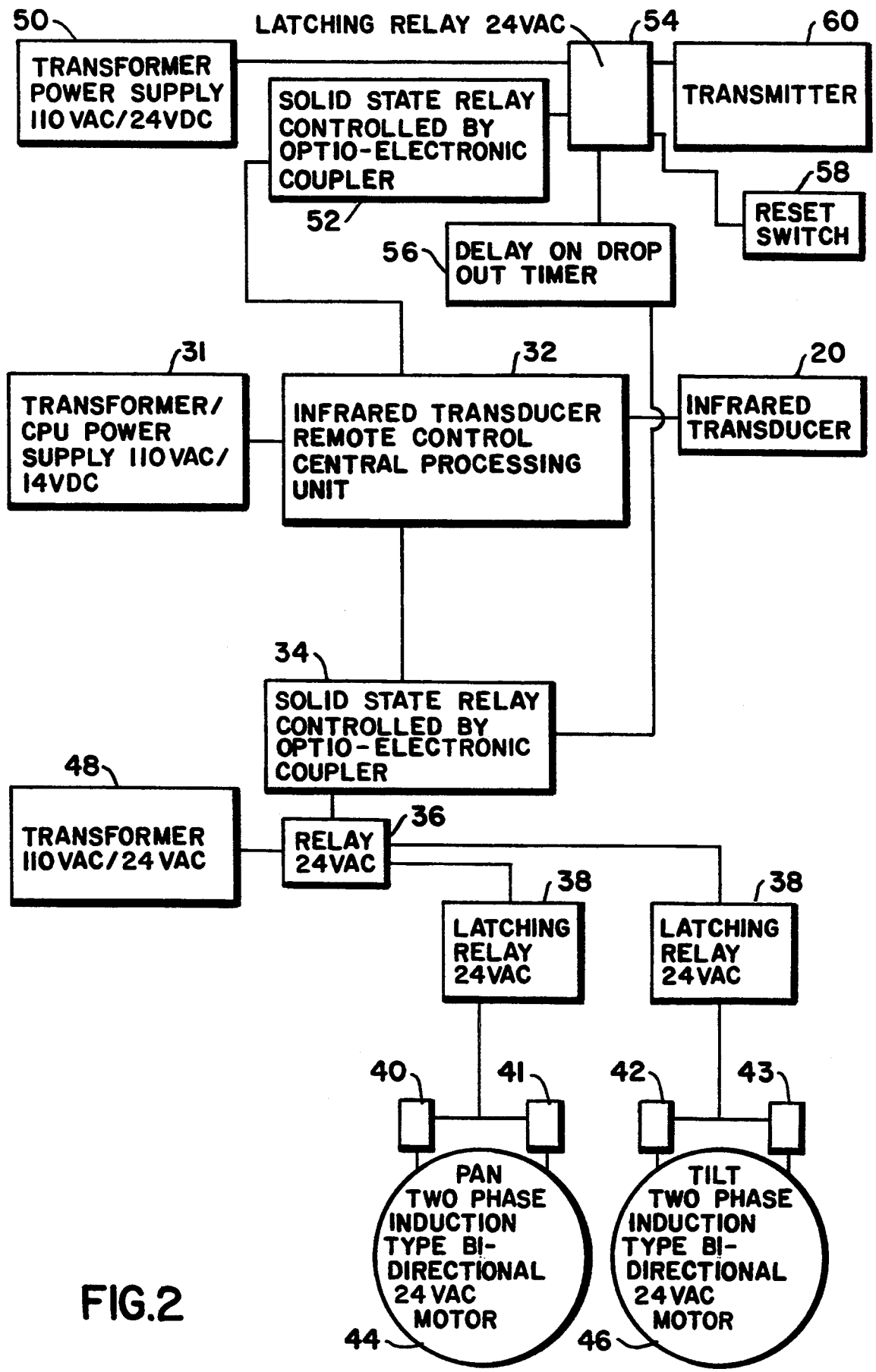
FIG. 2 is a schematic diagram of the apparatus.

The pan/tilt mechanism 22-10 is provided with adjustable limit switches for each drive to control the motion of each, and reverse direction when a predetermined point has been reached. As indicated in FIG. 2, the pan/tilt device 22-10 is operated by two 24 vac induction type bi-directional motors each of which rotates in one direction until a limit switch 40-43 is engaged which then energizes a latching relay 38, reversing the direction of the particular motor.

The infrared transducer 20 remote control central processing unit 32 is programmed with two temperature control set points. A minimal lower temperature of the target (patient) and a higher alarm tripping temperature.

When the transducer 20 detects the desired or (minimum) target temperature of the patient 6, the control unit 32 produces a 5 V DC signal which closes a solid state optio electronic relay 36 which in turn energizes the normally closed relays 38 opening the circuit to the pan/tilt motors 44 and 46. The pan/tilt motion ceases and the infrared transducer 9 remains focused on the target (patient).

If at any time when the infrared transducer 20 is focused on the patient 6 and the patient's temperature should increase above the second higher temperature a control set point produces a separate 5 VDC signal. This signal closes the solid state optio electronic relay 52 which closes the latching relay 54, permitting current to flow from the transformer 50 to the radio transmitter 60 sending a signal to a remote receiver (not shown) engaging in a loud-audio alarm and/or visual alarm to notify attending personnel of the rise in the patient's temperature.

A reset switch 58 is provided for personnel to disengage the latching relay 54 to shut off the alarm.

If the patient-target 6 moves out of the focus of the infrared transducer 20, the absence of 5 VDC signal from control unit 32 will deenergize the solid state relay 36 and allow the current from the 110/24 VDC transformer 48 to flow to the pan/tilt motors 44 and 46 causing the infrared transducer 20 to continue to scan the crib 4 area until the desired lower set point temperature is once again detected.

In the event that the lower set point temperature is not detected within a predetermined time, such as 5 minutes, in a case, for example, where the patient 6 has left the bed, an alarm is set off. Thus, if the delay on dropout timer 56 is not energized within 5 minutes, the relay 54 will engage and send current from the transformer 50 to the transmitter 60 to sound the alarm. The transformers 31-48 and 50 may be housed within a power box 25.

The central processing unit 32 can also transmit temperature data to a computer to obtain a detailed record of temperature events.

While the invention has been described by reference to an illustrative embodiment, it is not intended that the novel device be limited thereby, but that modifications thereof are intended to be included as falling within the broad spirit and scope of the foregoing disclosure, the following claims and the appended drawings.

What is claimed is:

1. A remote noninvasive patient temperature monitor and warning system comprising an infrared temperature transducer, a pan/tilt motor mechanism including a first electric drive motor for panning and a second electric drive motor for tilting, said infrared temperature transducer being mounted on said pan/tilt motor mechanism, a power circuit to said pan/tilt motor mechanism, said pan/tilt motor mechanism having adjustable limit switch means which control the range of motion of both pan and tilt motions and which reverse the respective drive motor direction for each of said pan and said tilt motions as said limit switch means are tripped, a remote control central processing unit receiving temperature information from said infrared transducer, said processing unit having means to store a first temperature value and a second temperature value higher than said first temperature value, means operable by a signal from said central processing unit to interrupt said power circuit to said pan/tilt motor mechanism when said first temperature value is reached and connect it when a lower temperature value is not detected, means operable by said central processing unit to connect a power source to an alarm device when said second temperature value is detected or when said first temperature value is not detected within a predetermined time period.

* * * * *